US005874297A

United States Patent [19]
Wu et al.

[11] Patent Number: 5,874,297
[45] Date of Patent: *Feb. 23, 1999

[54] SOLUBLE MOLECULAR COMPLEX FOR THE INTRODUCTION OF GENES INTO MAMMALIAN CELLS

[75] Inventors: George Y. Wu; Catherine H. Wu, both of Bloomfield, Conn.

[73] Assignee: University of Connecticut, Storrs, Conn.

[*] Notice: The term of this patent shall not extend beyond the expiration date of Pat. No. 5,166,320.

[21] Appl. No.: 690,510

[22] Filed: Jul. 31, 1996

Related U.S. Application Data

[63] Continuation of Ser. No. 368,757, Jan. 4, 1995, Pat. No. 5,635,383, which is a continuation of Ser. No. 901,919, Jul. 24, 1992, abandoned, which is a continuation of Ser. No. 504,064, Apr. 2, 1990, Pat. No. 5,166,320, which is a continuation of Ser. No. 39,934, Apr. 22, 1987, abandoned.

[51] Int. Cl.$^6$ .............................. C12N 5/00; C12N 15/00; A61K 48/00; C07K 1/00
[52] U.S. Cl. ................................... 435/320.1; 435/172.3; 514/44; 530/395; 935/52
[58] Field of Search .............................. 435/320.1, 172.3; 530/395; 514/44; 935/52

[56] References Cited

PUBLICATIONS

Ashwell et al. (1974), *Adv. Enzymol. Relat. Areas Mol. Biol.* 41:99–127.
Barrett (1968), "Properties of Lysosomal Enzymes", *Lysosomes in Biology and Pathology* 2:(10):245–312.
Gorman et al. (1982), "Recombinant Genomes Which Express Chloramphericol Acetyltransferase in Mammalian Cells", *Mol. and Cell. Biol.* 2(9):1044–1057.
Harford et al. (1981), "Immunological Evidence for the Transmembrane . . . for Asialoglycoproteins", *Proc. Natl. Acad. Sci. USA*, 78(3):1557–1561.
Klotz et al. ((1971), "Macromolecule–Small Molecule Interactions . . . Cross–Linked Polylysine". *Biochemistry* 10(6):923–926.
Li et al. (1973), *Biochem.* 12(9):1763–1772.
Ryser et al. (1982), "The Cellular Uptake of Horseradish Peroxidase . . . 900–Fold Difference in Rate", *Chemical Abstracts* 97:546.
Ryser et al. (1986), "Poly(lysaine): Heparin Complexes . . . Receptor–Mediated Endocytosis", *Chemical Abstracts* 105:355—356.
Stavridis et al. (1982), *Cell. and Molec. Biol.* 28:15–18.
Van der Sluijs (1986), "Drug Targeting to the Liver with Lactosylated . . . Targeting the Glycoprotein", *Hepatology* 6(4):723–728.
Wall et al. (1980), The Galactose–Specific Recognition System . . . in Rat Hepatocytes *Cell* 21:79–93.
Weiner et al. (1987), "Development of Molecular Hybridization . . . Baboons and Man", *Chemical Abstracts* 106:338.
Emlen et al. (1988), "Hepatic Binding of DNA is Mediated . . . Nonparenchymal Cells", *Amer. J. Path.* 133(1).
Wei–Chang et al. (1985), "Disulfide Spacer Between Methotrexate . . . Reductive Process in Endocytosis", *The Journ. of Biol. Chem.* 260(20):10915–10908.
Wu, et al. (Nov. 4, 1986), Abstract, *The American Associate for the Study of Liver Diseases*.
Wu et al. (1983), "Model for Specific Rescue of Normal Hepatocytes . . . Hepatic Malignancy", *Proc. Natl. ACED. Sci.* 80:3078–3080.
Wu et al. (1984), "Activity and Regulation of Low, Density Lipoprotein . . . Hepatoblastoma Cell Line", *Hepatology* 4(6):1190–1194.
Wu et al. (1985), "Acetaminophean Hepatotoxicity and Targeted Rescue . . . Hepatocellular Carcinomia", *Hepatology* 5(5):709–713.
Wu et al. (1987), "Receptor–Mediated in Vitro Gene Transformation by a Soluble DNA Carrier System", *Chemical Abstracts* 106:182.
Wu et al. (1987), "Receptor–Mediated in Vitro Gene Transformation by a Soluble DNA Carrier System", *Biological Abstracts* 84(1):AB–447.
Wu et al. (1987), *J. Biol. Chem.* 262:4429–4432.
Wu et al. (1988), "Evidence for Targeted Gene Delivery . . . Cells In Vitro", *Chem. Abstracts* 108.
Zenke et al. (1990), 87:3655–3659.

*Primary Examiner*—Deborah Crouch
*Attorney, Agent, or Firm*—Lahive & Cockfield, LLP; Jane E. Remillard; Giulio A. DeConti, Jr.

[57] ABSTRACT

A targetable gene delivery system is provided for introducing foreign genes into mamallian cells. The system employs a soluble targetable DNA complex and utilizes receptor-mediated endocytosis to endow cell specificity. The soluble DNA-carrying complex is formed by non-covalently binding a ligand conjugate with the foreign gene. The conjugate, in turn, is formed by bonding receptor-specific ligands such as asialoglycoproteins to polycations such as polylysine through covalent bonds such as disulfide bonds. The system exhibits a high degree of cell specificity and offers potential for the treatment of inherited genetic disorders.

11 Claims, 7 Drawing Sheets

COMPONENTS OF A TARGETABLE DNA COMPLEX

SOLUBLE MOLECULAR COMPLEX FOR THE INTRODUCTION OF GENES INTO MAMMALIAN CELLS

This application is a continuation application of Ser. No. 08/368,757, filed on Jan. 4, 1995, now U.S. Pat. No. 5,635,383 which is a continuation of Ser. No. 07/901,919 filed on Jul. 24, 1992, now abandoned, which is a continuation of Ser. No. 07/504,064 now U.S. Pat. No. 5,166,320 filed on Apr. 2, 1990, which is a continuation of Ser. No. 07/039,934 now abandoned, filed on Apr. 22, 1987. The contents of all of the aforementioned application(s) are hereby incorporated by reference.

BACKGROUND AND SUMMARY OF THE INVENTION

The present invention relates generally to the introduction of foreign genes into mammalian cells. More specifically, it relates to a new and improved carrier system and method for the non-invasive targeted delivery of soluble nucleic acid complexes to such cells.

The introduction of foreign genes into mammalian cells in vitro is frequently used for studying gene regulation. Various techniques for accomplishing this have been employed heretofore. The most popular method for this gene transformation employs a precipitation technique in which calcium phosphate is used as a coprecipitate with DNA to form insoluble particles. These particles, or at least some of them, become internalized within the host cells by endocytosis, resulting in the expression of the new or exogenous genes. This internalization is non-specific with respect to the cells of particular organs and does not rely upon any particular recognition site for the endocytosis. Although this technique is widely applicable in vitro, its use in vitro is limited by a lack of cell specificity, relatively low efficiency especially in certain highly differentiated cells. In addition, its use in vivo would be limited by the insoluble nature of the resulting precipitates. Other techniques also have problems. For example, viruses that have foreign genes incorporated within the viral DNA could be used either in vitro or in vivo. However, since the viral genes are also delivered simultaneously with the desired new gene, undesirable viral effects may be produced. As with the calcium phosphate precipitation technique, the use of viral agents is not generally specific for particular cell types.

Gene delivery also has been accomplished experimentally both in vitro and in vivo by using liposome entrapped DNA. Liposomes are small membrane-enclosed spheres that have been formed with the appropriate DNA trapped within. However, this system also has inherent problems. It is difficult to control the size of the liposome and, hence the uniformity of delivery to individual cells. Additionally, it is difficult to prevent leakage of the contents of the liposomes and, as with the other techniques, there has been difficulty in directing cell-type specificity. Electroporation and DEAE-dextran techniques are toxic to cells although a proportion of cells that survive are transformed.

Accordingly, it is an object of the present invention to provide a new and improved carrier system that can introduce foreign genes in a soluble non-toxic, cell-specific manner into mammalian cells. Included in this object is the provision for a system and method that exhibits a high degree of cell specificity using a relatively simple yet reliable delivery or carrier system. The solubility of the carrier system is a significant feature since it provides the possibility of targeting genes in vitro to a specific cell type present in a mixture of cell types. The present invention permits this without the necessity for simultaneously delivering viral genes and the undesirable viral effects that may be produced as a result thereof.

Another feature of the present invention is the use of receptor-mediated endocytosis to endow cell specificity to the gene delivery system. This involves the use of cell-surface receptors as naturally existing entry mechanisms for the specific delivery of genes. Included in this feature is the provision for a unique soluble polynucleotide complex capable of targeting the gene to specific cells possessing particular receptors that recognize the complex. The complex, in turn, employs a ligand conjugate as a new and improved carrier for DNA that can direct the complex to specific cell types having appropriate receptors.

A special feature of the present invention is the utilization of a specific type of non-covalent linkage provided by a component of the conjugate for binding polynucleotides electrostatically to the conjugate in a non-damaging fashion. An additional feature is the coupling of the polynucleotide binding component to a ligand by a bond that can result in facile cleavage from the ligand following internalization.

These features and advantages of the present invention all directly contribute to the efficiency and targetability to specific cell types, including normal cells as well as hepatoma cell systems, and form the basis for in vitro delivery in an efficient and effective manner while avoiding the disadvantages of prior systems. The provision of a soluble gene delivery system is particularly attractive for the study of how genes are controlled in vitro and in vivo. In addition, by virtue of its solubility and targetability, this system may have potential for replacement of defective genes as treatment for inherited genetic disorders in vivo.

Other features and advantages will be in part obvious and in part pointed out more in detail hereinafter.

These and related advantages are achieved in accordance with the present invention, by providing a new and improved soluble polynucleotide carrier system based on the use of cell surface receptors or binding sites that recognize and internalize certain specific biological compounds or molecules. This internalization process, known as endocytosis, is a normal biological function and the method of the present invention provides a system whereby soluble polynucleotide complexes utilize this specific targeted receptor-mediated endocytotic mechanism.

A better understanding of the features and advantages of the present invention will be obtained from the following detailed description and the accompanying drawing as well as from the illustrative applications of the invention. This includes the several components of the invention and the relation of one or more of such components with respect to each of the others and the process including the several steps thereof and their relationship with each of the others as well as the features, characteristics, compositions, properties and relation of elements described and exemplified herein.

BRIEF DESCRIPTION OF THE DRAWINGS

In the drawings:

FIGS. 2(A–B) is a photograph of an autoradiograph used to determine the conjugate to DNA ratio that maximizes the DNA content in the complex.

DESCRIPTION OF A PREFERRED EMBODIMENT

It is known that most, if not all, mammalian cells possess cell surface binding sites or receptors that recognize, bind and internalize specific biological molecules, i.e ligands. These molecules, once recognized and bound by the receptors, can be internalized within the target cells within membrane-limited vesicles via receptor-mediated endocytosis.

It is also known that DNA molecules consist of large negatively charged polynucleotide chains that do not enter cells by simple exposure to the cells. For this reason the techniques mentioned hereinbefore, such as the use of viruses, liposome carriers, calcium coprecipitation etc., are required to achieve introduction of foreign DNA. Accordingly, the present invention provides a mechanism whereby a polynucleotide (PN) is attached to an appropriate ligand in such a way that the combination thereof or complex remains soluble, is recognized by the receptor and is internalized by the cell. The PN is carried along with the ligand into the cell, subsequently resulting in the expression of the foreign or exogenous gene and potentially correcting certain biological or cell defects. The soluble complex must, however, bind or hold the PN to the ligand without in any way damaging or chemically altering the gene, and without functionally altering the ligand so it is no longer recognizable by the receptor.

Figure 1:
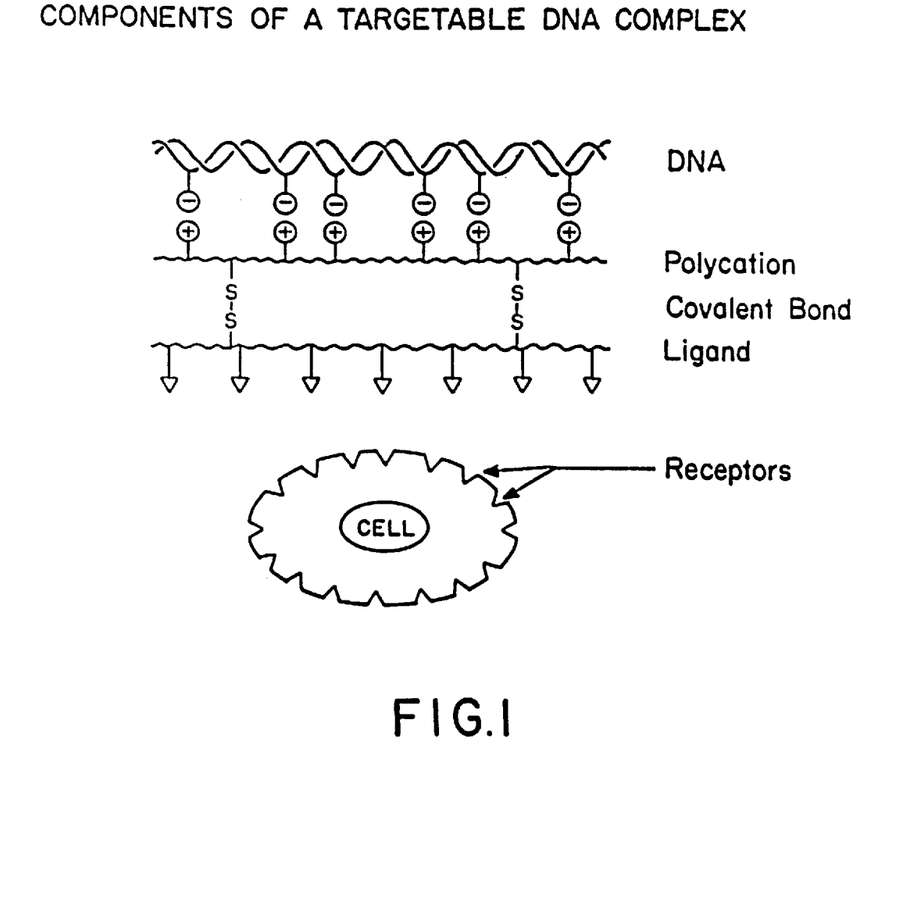
FIG. 1 is a schematic illustration of the technique of the present invention for introducing foreign genes into mammalian cells and shows, in general, the make-up of the soluble complex and conjugate of the new delivery system.

As schematically illustrated in FIG. 1, this is achieved in accordance with the present invention by providing a carrier system comprising a conjugate that forms a soluble complex with the PN. The conjugate comprises a ligand that is receptor-specific for a particular mammalian cell and a PN-binding component covalently bonded to the receptor-specific ligand. The PN-binding component, as indicated, must be capable of complexing with the PN without damaging or chemically altering the gene and also must be capable of being securely bonded to the ligand through a bond that can be easily cleaved after endocytosis. In our invention, the bond between the PN-binding component and the PN is a non-covalent bond but is based on electrostatic attraction of the opposite charges present on the PN and the PN-binding component. The bond between the PN-binding component and the ligand is a covalent bond. Both bonds are of sufficient strength to prevent uncoupling prior to endocytosis yet are easily cleaved under appropriate conditions within the cell.

Thus, as can be appreciated, the method of the present invention utilizes cell surface receptors as naturally existing entry mechanisms for the specific delivery of genes to selected mammalian cells. Additionally, the soluble PN complex targets PN to those cells possessing the particular receptors that recognize the ligand thereby assuring targeted delivery of the PN to specific cell types.

VARIABLES THAT GOVERN OPTIMAL GENE TARGETING

A. PN-binding components

As mentioned, genes, the ultimate source of biological information, cannot be expressed by simple exposure to cells due to the size and the negative charges of the PN molecules. In accordance with the present invention, coupling of the gene to a carrier conjugate containing a ligand will provide a soluble complex that can result in internalization and expression of the gene. Of course, in order to provide the requisite successful internalization of the gene, it is necessary that the coupling or linkage between the PN and the carrier conjugate be such that the coupling process does not damage or alter the gene. This is achieved in accordance with the present invention by utilizing a PN binding component that takes advantage of the negative charge on the PN chain and coacts therewith to tightly bind with the positive charges of the PN-binding agent while avoiding covalent bonding that might chemically alter the gene. In accordance with the present invention this is achieved through the use of polycations that bind to the negatively charged PN chain. These strongly positively charged polycations provide secure, tight complexing in a non-covalent manner to form the desired soluble targetable complex between the conjugate containing the coupling agent and the PN chain. The polycations used as coupling agents to "glue" the complex together and hold the PN during internalization may be materials such as polylysine, polyarginine, polyornithine, basic proteins such as histones, avidin, protamines and the like. Other similar materials may be used.

Other non-covalent bonds that could be used consistent with our non-deforming linkage strategy would include but not be limited to hydrogen bonding, hydrophobic bonding, electrostatic bonding alone or in combinationas in: anti-DNA antibodies (immunoglobulins) bound to DNA, strepavidin or avidin binding to DNA containing biotinylated nucleotides etc.,.

B. Proportions of PN and Conjugate

Figure 2A:
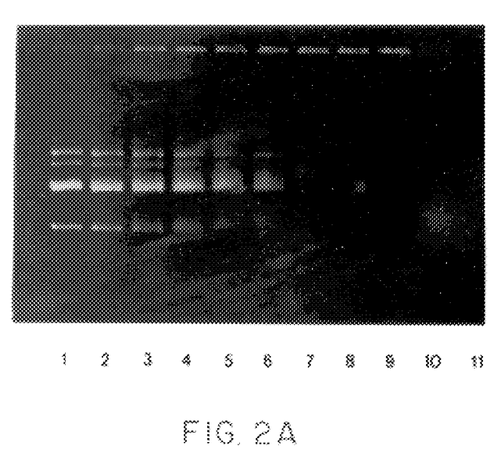
Figure 2B:
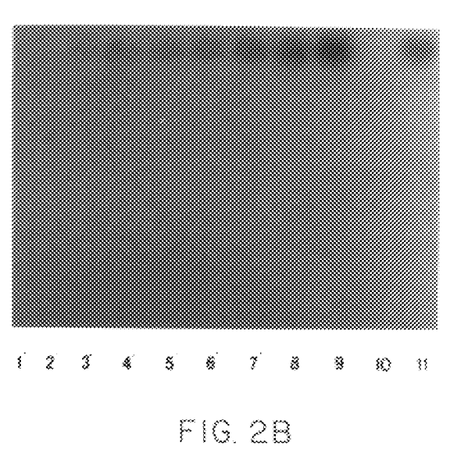

The relative amounts of the PN and the conjugate effective to form a soluble complex may vary considerably. However, it is preferred that the molar ratio of the conjugate to the PN fall within the broad range from about 1:10 to about 10:1 to ensure that the resultant complex is soluble. In this connection it has been found that the maximal ratio of conjugate to PN that leaves no DDNA uncomplexed typically falls within the range of 1:5 to 5:1 and preferably within the range of 1:2 to 3:1. FIG. 2 shows the effect of increasing proportions of asialoorosomucoid(AsOR)-polylysine conjugate on complex formation with plasmid pSV2 CAT DNA: changes in DNA migration through a 0.8% agarose gel. In panel A, increasing amounts of $^{125}$I-AsOR-polylysine conjugate in high salt (2M NaCl) to constant amounts of DNA samples (also in 2M NaCl). After incubation for 1 hr, the mixtures were dialyzed against 0.15M NaCl, Millipore filtered and electrophoresed through a 0.8% agarose gel and stained with ethidium bromide to visualize the DNA. Lane 1 contains DNA alone while lanes 2 through 9 have DNA with progressively increasing proportions of conjugate:

| Lane | Conjugate/DNA Ratio | Lane | Conjugate/DNA Ratio |
|---|---|---|---|
| 1 | 0 | 6 | .92 |
| 2 | .12 | 7 | 1.15 |
| 3 | .23 | 8 | 1.40 |
| 4 | .46 | 9 | 1.84 |
| 5 | .69 | | |

Lane 10 contains saline and lane 11 contains the conjugate $^{125}$I-AsOR-polylysine. Panel B shows the same lanes after the agarose gel was dried and autoradiographed to detect $^{125}$I-AsOR-polylysine conjugate. The DNA content in a complex is maximized for this particular conjugate at a conjugate to PN ratio between 1.15:1 (lane 7) and 1.40:1 (lane 8). It will be appreciated that the optimal ratio may be different for other genes and other conjugates containing different polycation compositions. Further, with certain complexes it may be necessary to increase the proportion of ligand, e.g. AsOR, in the conjugate so that more of the particular ligand is exposed for recognition by the appropriate cell receptor.

C. Bonds between the ligand and the PN-binding Component

In order to utilize the non-covalent coupling of the polycations with the polynucleotide chain, it is necessary to form a conjugate of the cationic coupling agent (polycation) and the appropriate ligand. This has been achieved through the formation of an easily cleaved bond between the polycation and the ligand. In this connection a chemical covalent bond such as a disulfide bond between the polycation and the ligand has been found to produce excellent results. Of course, other covalent bonds such as amide or peptide bonds could be utilized but may be relatively more resistant to cleavage.

D. The Proportion of Ligand to PN-binding Component in the Targeted Conjugate

When forming this bond varying amounts of the polycation and ligand may be used depending on the specific materials employed. When using polylysine as the polycation and a glycoprotein containing exposed galactose residues, an asialoglycoprotein, as the ligand, ratios greater than 1:3, such as ratios of 20:1 to 1:1 can be used. In this connection, ratios of conjugate to polycation of 4:1 to 7:1 have been found effective for conjugates specific to hepatocytes.

E. The Nature of the Ligand

As mentioned, this specific targeted delivery of genes to individual mammalian cells using a soluble carrier system is based on the fact that most if not all mammalian cells possess certain surface binding sites, referred to as receptors, that recognize and internalize specific ligands. Typically these ligands are proteins having functional groups that are exposed sufficiently to be recognized by the cell receptors. The particular proteins used will vary with the particular target cell. Typically glycoproteins having certain exposed terminal carbohydrate groups are used although other ligands such as antibodies or polypeptide hormones, also may be employed. For specific targeting to hepatocytes (liver cells), asialoglycoprotein (galactose-terminal) ligands may be formed by chemical or enzymatic desialylation of those glycoproteins that possess terminal sialic acid and penultimate galactose residues. Alternatively, hepatocyte-targetable asialoglycoprotein ligands may be created by coupling lactose to non-galactose-bearing proteins by reductive lactosamination.

Because a variety of different receptors exist on the surfaces of mammalian cells, cell-specific targeting to other (non-hepatic) cells may be possible based on the use of other ligand components i.e mannose-6-phosphate glycoproteins for fibroblasts, intrinsic factor - Vit $B_{12}$ for enterocytes, insulin for fat cells, etc.,.

POTENTIAL PROBLEMS AND REASONABLE SOLUTIONS

It is possible that in a mixed population of cells in vivo, scavenger cells might reduce the specificity of this system by the non-specific uptake of the soluble complex. This can be avoided in various ways. For example, ligands having a higher affinity for their particular receptor may be used. Non-specific uptake may be blocked with agents such as dextran sulfate, or the proportion of ligand in the complex may be increased so that more ligand is exposed for recognition.

For purposes of illustration only, and so that the invention can be more readily understood, the invention will be described hereinafter primarily with respect to liver cells, hepatocytes, since these cells possess unique receptors that bind and internalize galactose-terminal (asialo-) glycoproteins (AsG). The following specific examples are given for the purpose of illustration only, in order that the present invention may be more fully understood. These examples are not intended to in any way limit the practice of the invention. Unless otherwise specified all proportions are expressed as molar ratios.

EXAMPLE I: Evidence for Formation of a ASG-PL-DNA Complex; Method for Maximization of DNA Content In a Targetable Complex The protein, orosomucoid, was prepared from pooled human serum and was converted to an AsG by exposing its galactose residues to form asialoorosomucoid (AsOR). It was determined to have no residual sialic acid and then labeled with iodine 125 using carrier-free Na $^{125}$I. It was then conjugated to polylysine (PL) (molecular weight 50,000–100,000 daltons) in a molar ratio of 7 to 1 via disulfide bonds using N-succinimidyl 3-(2 pyridyldithio) propionate to form the labeled conjugate, $^{125}$I-AsOR-PL. The conjugate was separated from noncoupled $^{125}$I-ASOR and poly-L-lysine on a Bio-Gel A-1.5 m column (Bio-Rad) eluted with 0.01M HEPES, 2M guanidine HCl, pH 7.4. The conjugate peak was identified as that containing both $^{125}$I radioactivity and a lysine content in excess of that contributed by ASOR alone as determined by amino acid analysis after hydrolysis in 6N HCl at 100° C. for 24 h. From the specific activity of $^{125}$I-ASOR and the lysine content of the conjugate, the molar ratio of ASOR to poly-L-lysine in the conjugate was calculated to be 7:1. The conjugate was found to be stable at −20° C. for at least 4 months. A 10% sodium dodecyl sulfate-polyacrylamide gel of the conjugate after electrophoresis, stained with Coomassie Blue, revealed a single band which, in the presence of mercaptoethanol, completely resolved the conjugate into its asialoorosomucoid and poly-L-lysine components.

In order to determine the optimal proportion of DNA to mix with the conjugate to form a soluble complex, samples containing equal amounts of DNA in 2M NaCl were mixed with increasing amounts of the labeled conjugate in 2M NaCl. Each sample was incubated for one hour at 25° C. and the mixtures were dialyzed for 24 hours against 0.15M saline through a membrane with an M.W. limit of 3500. Although clear solutions were obtained after dialysis, all samples were Millipore filtered through 0.2 um membranes to ensure that the complex to be used was soluble. An aliquot of each sample was heat-denatured and the DNA content was measured fluorometrically. There was no significant loss of DNA due to the filtration step. The $^{125}$I-AsOR-PL-DNA samples were loaded onto an 0.8% agarose gel for electrophoresis at 50 V for three hours. Ethidium bromide stain was used in Panel A of FIG. 2 to visualize the DNA and an autoradiogram of the same gel after drying was obtained at −70° C. as shown in Panel B to detect the conjugate. Electrophoresis of only the conjugate showed a single band that did not migrate from the top of the gel, as shown in lane 11' of FIG. 2, Panel B. Ethidium bromide staining showed that the DNA alone normally enters the gel forming discrete characteristic bands, see lane 1 of FIG. 2, Panel A. However, as the proportion of conjugate added to the DNA in the samples increased, Panel A lane 2 through lane 9, there was a decrease in staining intensity of DNA bands in the gel and a corresponding increase in staining of DNA that did not migrate, remaining at the top of the gel with the conjugate. This indicates that progressive amounts of DNA were bound with increasing proportions of conjugate. The graphic showing in FIG. 2 illustrates that for this conjugate, a conjugate to DNA ratio of between 1.15:1 (lane 7) and 1.40 (lane 8) was found to maximize complex formation for the specific materials used.

EXAMPLE II: Determination of Conjugate to DNA Proportions Necessary to Create Soluble Complexes To confirm the increase in DNA content of complexes formed by addition of increasing amounts of conjugate to DNA samples and to determine the proportions that limit solubility of complexes, DNA was first labeled with $^{32}$P by nick-translation. The protein, orosomucoid, was converted into an AsG by exposing its galactose residues to form asialoorosomucoid (AsOR). After purification, AsOR was conjugated to polylysine (PL) in a molar ratio of 5 to 1 as described in Example I. Constant amounts of labeled DNA were mixed with increasing amounts of unlabeled conjugate (AsOR-PL) and filtered as described in Example I. The filters were counted for $^{32}$P radioactivity to measure insoluble DNA if present.

The filtrate was electrophoresed on an agarose gel as described in Example I. After drying, an autoradiogram was obtained and the corresponding radioactive bands of the gel were cut out and counted.

Figure 3:
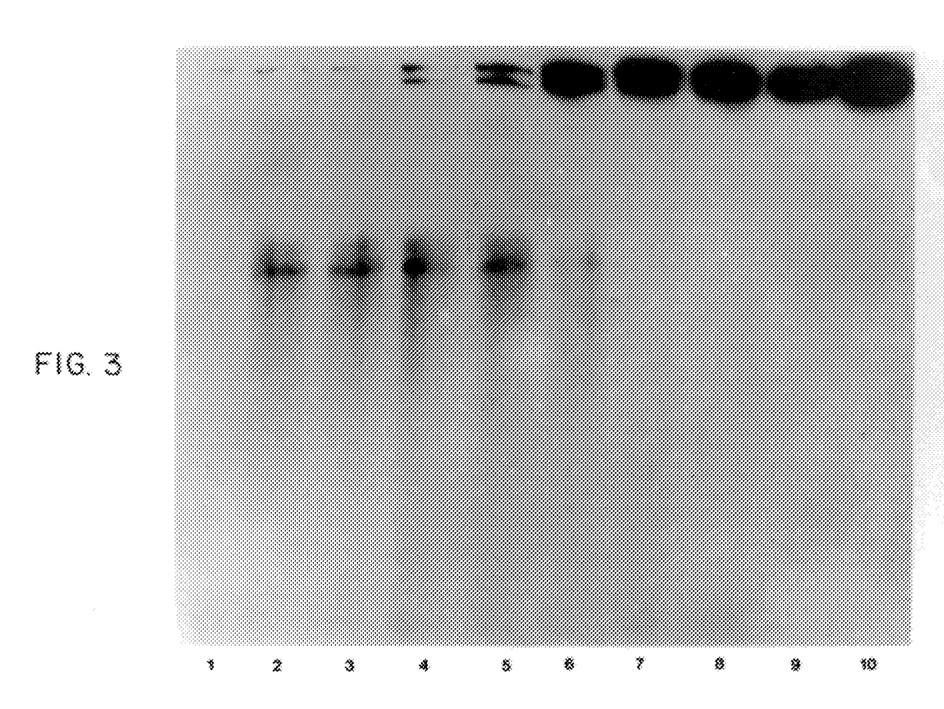
FIG. 3 is a photograph of the electrophoretic migration of DNA samples illustrating the relationship between the mobility of the complex and the ratio of conjugate to DNA in the complex.

Counting of the filters showed that addition of increasing amounts of conjugate to the DNA samples did not result in any significant insoluble DNA until a conjugate to DNA ratio of greater than 3.27:1 was reached, see Table I. The data for this measurement as shown in Table I permitted determination of this limiting molar ratio above which the conjugate-DNA complex became insoluble. Examination of the radioactive bands on the agarose gel, FIG. 3, confirmed that as the proportion of conjugate to DNA increased up to a ratio of approximately 2.34:1 (lane 7)

TABLE I

| Lane | Conjugate/DNA Molar Ratio | Filter (cpm) | Supernatant (cpm) |
|---|---|---|---|
| 1 | 0 | 8,437 | 79,936 |
| 2 | .23 | 7,933 | 85,914 |
| 3 | .47 | 7,746 | 88,097 |
| 4 | .94 | 8,546 | 85,332 |
| 5 | 1.40 | 7,941 | 84,761 |
| 6 | 1.87 | 8,728 | 82,521 |

TABLE I-continued

| Lane | Conjugate/DNA Molar Ratio | Filter (cpm) | Supernatant (cpm) |
|---|---|---|---|
| 7 | 2.34 | 8,746 | 85,332 |
| 8 | 2.80 | 8,476 | 82,428 |
| 9 | 3.27 | 8,540 | 85,446 |
| 10 | 3.55 | 15,083 | 78,903 |
| 11 | 3.88 | 45,526 | 50,317 |
| 12 | 6.09 | 72,528 | 18,376 |
| 13 | 9.13 | 85,244 | 6,005 | more DNA became complexed with conjugate at the top and less entered the gel. The data shown in Table I and graphically depicted in FIG. 3 indicates that for this conjugate, the DNA content of the soluble complex is maximized at a conjugate to DNA ratio of between 1.87:1 (lane 6) and 2.34:1 (lane 7). This ratio is different from that obtained in Example I because the AsOR and PL composition of this conjugate was different from that used in Example I. This serves to illustrate that the optimal proportions for the preparation of soluble complexes with maximal DNA content may vary depending on the composition of the conjugate and the nature of the DNA used.

EXAMPLE III: Evidence for Targeted Gene Delivery

The AsOR-PL conjugate (AsOR to PL ratio of 5:1) was complexed with a suitable piece of DNA with a resultant molar ratio of 2.34:1 and Millipore filtered. The DNA was in the form of a bacterial plasmid, pSV2 CAT, which contains the gene for the bacterial enzyme chloramphenicol acetyl transferase (CAT). The bacterial enzyme CAT catalyzes the acetylation of the antibiotic chloramphenicol. The plasmid was grown in *Escherichia coli*, isolated and purified. The purity was confirmed by 0.8% agarose gel electrophoresis, demonstrating an absence of bacterial cellular DNA. The plasmid, containing the CAT gene and an SV-40 promoter to allow expression in mammalian cells, was used in forming the complex AsOR-PL-pSV2 CAT. Since mammalian cells lack the gene for forming the enzyme CAT, the appearance of CAT enzyme activity in the target cells can be used as a convenient marker of gene transformation.

To test targeted gene delivery using the soluble complex, two human hepatoma cell lines were used. The first cell line was Hep G2 (AsG receptor-positive) representing normal hepatocytes obtained from B. Knowles, Wistar Institute, Philadelphia, Pa., while the second was SK Hep 1 (receptor-negative) cells obtained from D. Shafritz, A. Einstein College of Medicine, Bronx, N.Y. Each cell line was separately grown to one - quarter confluence and then incubated at 37° C. for 48 hours under 5% $CO_2$ in medium containing the conjugate-plasmid complex or controls consisting of the plasmid alone (520 pM DNA), the plasmid plus 1.04 nM AsOR and the plasmid plus 200 pM PL. In each control, the components were added in the same concentrations and proportions as present in the complex.

Figure 6A:
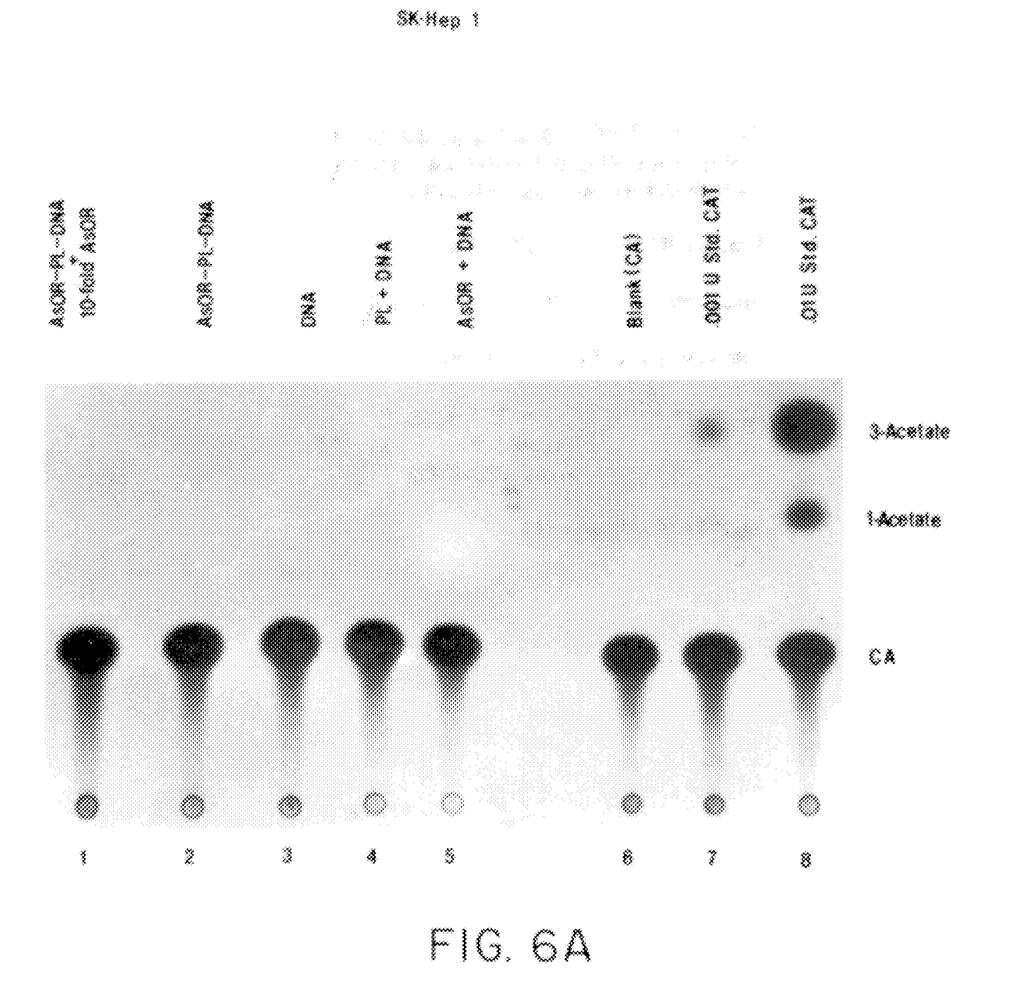
FIG. 6A is a photograph of an assay for gene transformation in a receptor negative cell line.
Figure 6B:
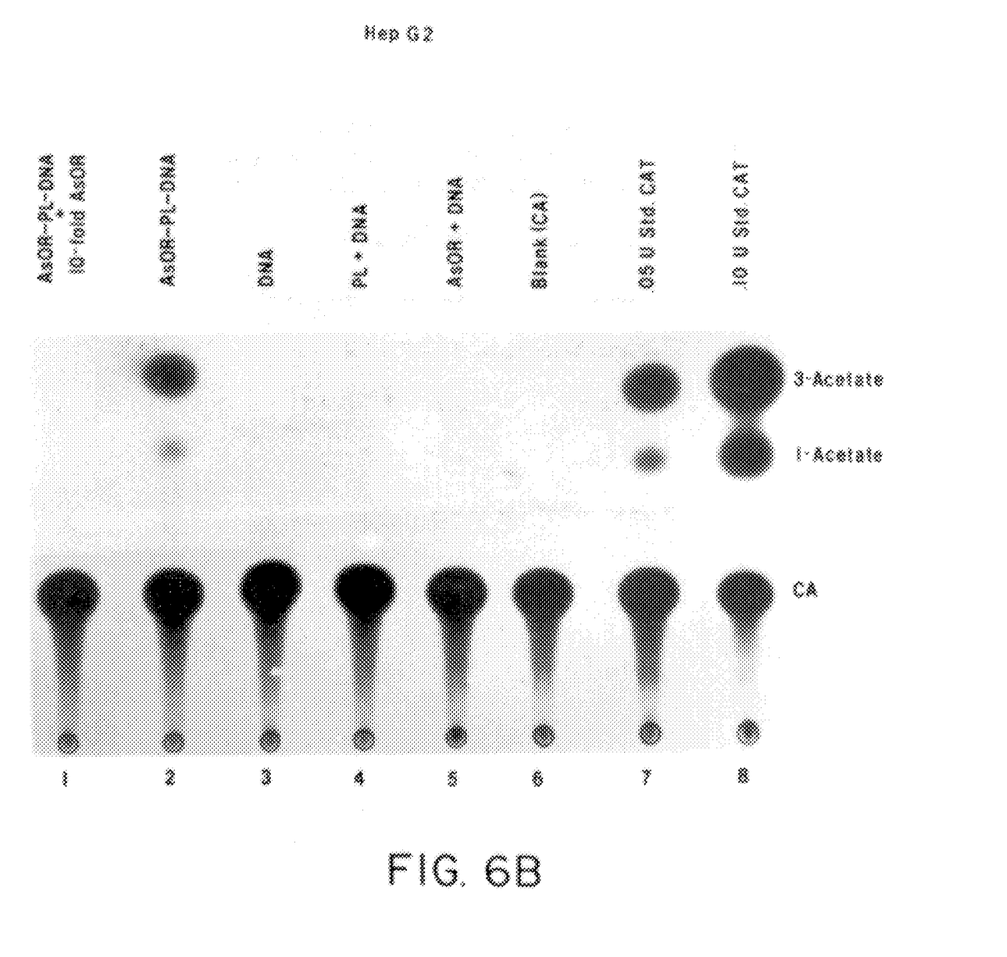
FIG. 6B is a photograph of an assay for gene transformation in a receptor positive cell line.

To assay for CAT activity, medium was aspirated and the cells were washed with ice-cold phosphate-buffered saline, were sonicated for 1 minute, centrifuged at 10,000 rpm for 10 minutes at 4° C. and the supernatants incubated at 25° C. with $^{14}$C-chloramphenicol. Enzyme activity was detected by the presence of 1- or 3- acetyl chloramphenicol derivatives. Cell extracts spotted onto thin layer chromatographic plates were developed using a 95:5 (by volume) mixture of chloroform and methanol and, after drying, exposed to photographic film. As shown in FIG. 6A no activity was found in the SK Hep 1 (receptor-negative) cells under any condition. However, as seen in FIG. 6B, Hep G2 (receptor-positive) cells that received the complex (lane 2) produced readily detectable CAT activity (0.025 Units)/$10^7$ cells. Control Hep G2 cells exposed to the plasmid alone (lane 3), the plasmid plus PL (lane 4), or the plasmid plus ASOR (lane 5) showed no detectable activity and, therefore, were not transformed by separate components of the targeted complex.

A control in lane 1 using a ten-fold excess of AsOR inhibited transformation and expression of CAT, thereby supporting the thesis that recognition of the complex is directed by the AsOR component of the conjugate.

As additional controls to prove the specificity of the targeted gene delivery system, other hepatic and non-hepatic cell types (that do not possess the asialoglycoprotein receptor), human fibroblasts, smooth muscle cells, hepatoma cells were incubated with the complex under identical conditions. None of those cells were transformed as determined by the CAT assay.

EXAMPLE IV: Evidence for Targeting Genes Specifically to Xepatocytes in a Mixture of Cell Types in vitro.

Figure 4:
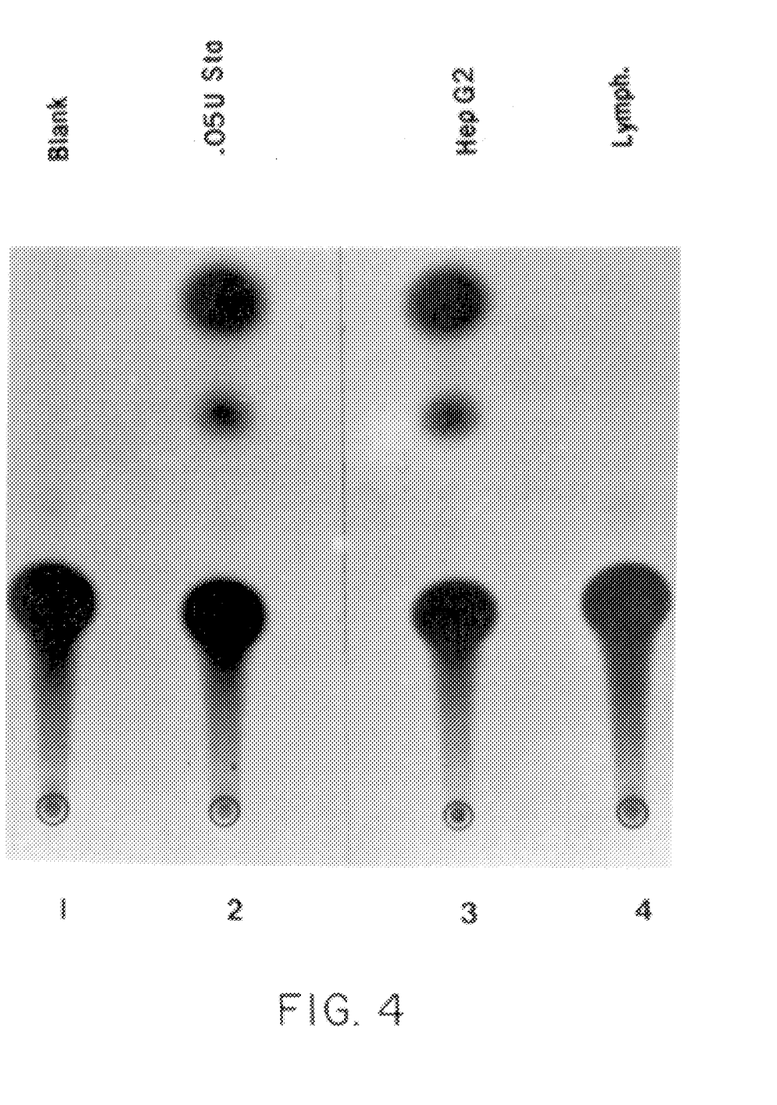
FIG. 4 is a photograph of an autoradiograph showing the targeted gene transformation of only hepatocyte-derived receptor (+) cells in a mixed co-culture of hepatocyte-derived and non-hepatocyte derived cells.

Hep G2, asialoglycoprotein AsG receptor (+), hepatocyte-derived cells were co-cultured with WFu-Gl lymphocyte-derived, AsG receptor (−) cells (from D. Greiner, Univ. of Connecticut, Farmington, Conn.) to one-quarter confluence. The medium was then changed to contain ASOR-PL-DNA complex at the same concentration that was successful in transforming Hep G2 cells alone. Because the lymphocyte-derived cells do not adhere to plastic plates as do the hepatocyte-derived cells, the lymphocyte-derived cells could be separated by simply washing the cells from the dishes with buffer. After 48 hours of incubation with the complex, the lymphocyte-derived (non-adherent) cells were washed from the dishes of adherent hepatocyte-derived cells. Microscopic inspection revealed that the separation of the two cell types was complete (less than 1% contamination). Hepatocyte-derived cells were subsequently scraped from the dishes. Each cell type was centrifuged, sonicated, then assayed for CAT activity using $^{14}$C-chloramphenicol as described before in Example III. FIG. 4, lane 1 contains $^{14}$C-chloramphenicol alone, lane 2, 0.05 U CAT standard. From FIG. 4, lane 3, Hep G2, hepatocyte-derived, receptor (+) cells, demonstrated formation of acetylated chloramphenicol derivatives 0.022 CAT Units/$10^7$ cells, indicating that they had been transformed by our system. However, no CAT activity was detected in the non-hepatocyte (lymphocyte-derived) receptor (−) cells FIG. 4, Lane 4. These cells were not transformed under identical co-culture conditions indicating that the soluble gene targeting system was specific for hepatocyte-derived cells and can be used to deliver genes to target cells, within a cell mixture, by a cell-specific, discriminating manner.

EXAMPLE V. Targeted Gene Delivery to Normal Hepatocytes in vitro.

Figure 5:
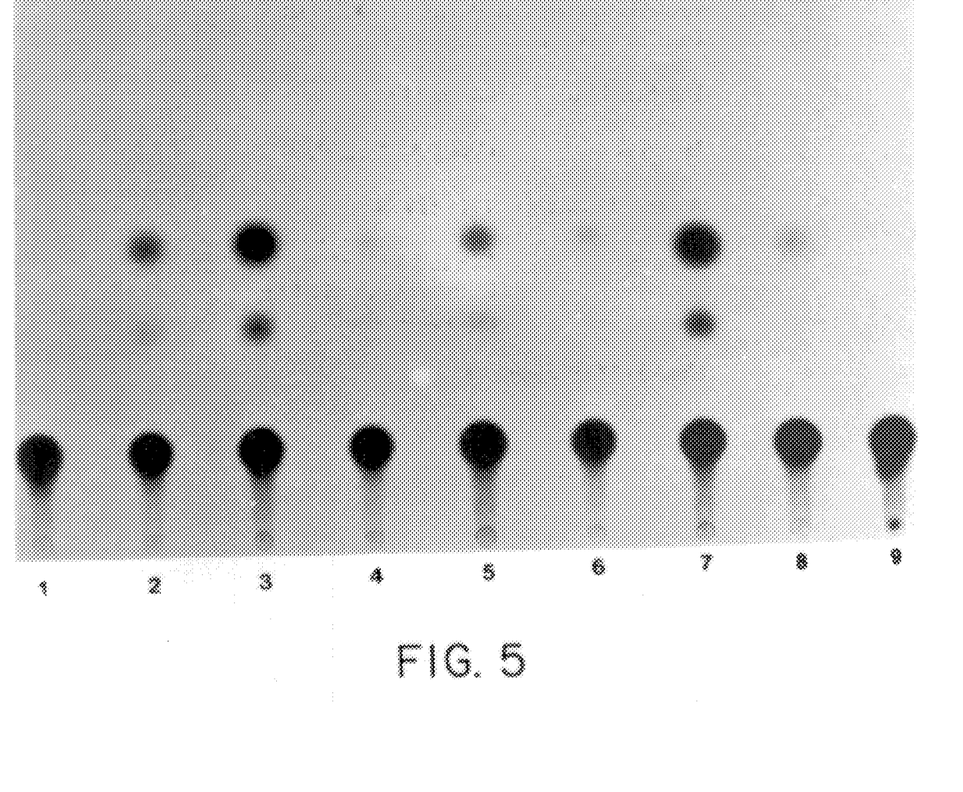
FIG. 5 is a photograph of an autoradiograph showing the efficiency of gene trasnformation of isolated normal rat hepatocytes by our soluble targetable gene delivery system.

In order to determine whether our soluble gene targeting system could deliver genes to normal hepatocytes as well as our model receptor (+) hepatoma cell line (Hep G2), normal adult Sprague-Dawley rat livers were sterilely perfused in situ with a collagenase-containing solution and hepatocytes isolated sterilely. Contamination by non-hepatocyte cells was less than 10% as determined by microscopic inspection. Hepatocytes, thus obtained, were plated on plastic dishes and allowed to attach for 24 hours in serum-containing medium. The medium was then changed to defined medium (without serum) plus AsOR-PL-DNA complex containing the CAT gene. Cells were incubated for an additional 24 hours to allow uptake of the complex. The number of viable cells present was found to be unchanged by the incubation. To determine whether any of these cells expressed the foreign DNA, cells were scraped from the dishes, sonicated, and incubated with $^{14}$C-chloramphenicol and assayed for CAT activity as described in Example III. This data is shown in FIG. 5 with lane 1 containing $^{14}$C-Chloramphenicol alone. Lane 2 has 0.01 Units CAT standard while 0.05 Units CAT are in lane 3. Hepatocytes treated with AsOR-PL-DNA complex: 0.5 mg hepatocytes are in lane 4; 2 mg hepatocytes in lane 5; and complex-treated hepatocytes, 2 mg assayed in the presence of enzyme inhibitors: phenylmethylsulfonyl fluoride (PMSF) and N-ethylmaleimide (NEM) in lane 6; in the presence of PMSF and ethylene diamine tetraacetic acid (EDTA) in lane 7; or in the presence of PMSF, EDTA and NEM in lane 8. Hepatocytes without previous exposure to AsOR-PL-DNA complex are in lane 9. Acetylated derivatives of chloramphenicol were easily detectable with an apparent efficiency of gene transformation of 0.005 CAT Units/mg cells, FIG. 5, lanes 4 and 5. However, because normal hepatocytes contain numerous proteolytic enzymes that could interfere with CAT enzyme function, CAT assays were also performed in the presence of enzyme inhibitors PMSF and EDTA, lane 7. This shows that the actual efficiency of gene transformation in isolated hepatocytes was on the order of 0.025 CAT Units/mg cells. The agent, NEM, inhibits CAT activity as shown in lanes 6 and 8. Control (hepatocytes not previously exposed to complex) lane 9 did not produce acetylated chloramphenicol derivatives. These controls serve to confirm that non-transformed isolated hepatocytes do not inherently possess CAT or CAT-like enzymatic activity.

The fact that the difference in number of viable cells before and after incubation with the targetable complex was less than 10% indicates that the complex was not toxic to the normal isolated hepatocytes.

This data indicates that freshly isolated normal hepatocytes can be transformed with foreign genes by our delivery system. Furthermore, the lack of significant change in the number of viable cells before and after incubation with complex indicates that our soluble complex is not toxic to the recipient cells.

EXAMPLE VI: Targeting of DNA specifically to Liver in Vivo.

AsOR-PL-DNA complex containing $^{32}$P-labelled psv2 CAT in saline was Millipore filtered, and then injected intravenously into adult rats. After 15 minutes, the animals were sacrificed and organs removed, samples homogenized and counted for $^{32}$P radioactivity. The results indicate that the complex was rapidly removed from blood. Only 4.5% of the injected radioactivity remained in blood after 15 minutes with a half-life of less than 10 minutes. Approximately 75% of the injected counts was found in the liver. This pattern of uptake is similar to that described for non-conjugated asialoglycoproteins suggesting that the complex, like asialoglycoproteins, is targeted to liver asialoglycoprotein receptors.

Thus, it is clear that by coupling the AsG to the PL and mixing the plasmid therewith, a soluble protein-DNA complex was formed. This complex introduced the DNA into cells possessing the receptor for the protein and the exogenous DNA functioned within the target cell to produce the new gene product.

In these specific examples, particular ligands have been used since they are recognized by liver cells. However, many other ligands could be used to target genes to other cells such as fibroblasts or reticuloendothelial cells based on the presence of different receptors on those cells. Here too, because of the solubility and targetability of our system, the method may be of value not only in the delivery of genes in vitro but also in vivo. Targeting of genes to stable, long-lived cell types e.g., hepatocytes raise the possibility of replacing defective genes responsible for inherited metabolic disorders such as but not limited to hemophilia, Lesch-Nyhan, Von Gierke's, Her's, Pompe disease etc.

As will be appreciated by those skilled in the art, various modifications, adaptations and variations of the foregoing specific disclosure can be made without departing from the teaching of the present invention.

We claim:

1. A molecular carrier suitable for forming a complex with a polynucleotide, the carrier comprising:
   (a) a ligand specific for a receptor of a mammalian cell, wherein the receptor binds to and internalizes the ligand; and
   (b) a polycationic binding agent capable of forming a complex with a polynucleotide.

2. The molecular carrier of claim 1 wherein the polycationic binding agent is polylysine.

3. The molecular carrier of claim 1 wherein the ligand binds to the asialoglycoprotein receptor present on hepatocytes.

4. The molecular carrier of claim 3 wherein the ligand is an asialoglycoprotein.

5. The molecular carrier of claim 1 wherein the polycationic binding agent is bonded to the ligand by a covalent bond.

6. A molecular complex for delivering a polynucleotide to a cell, the complex comprising:
   (a) a molecular carrier comprising a ligand specific for a receptor of a mammalian cell, wherein the receptor binds to and internalizes the ligand, and a polycationic binding agent; and
   (b) a polynucleotide complexed to the molecular carrier via the polycationic binding agent.

7. The molecular complex of claim 6 wherein the polycationic binding agent is polylysine.

8. The molecular complex of claim 6 wherein the ligand binds to the asialoglycoprotein receptor present on hepatocytes.

9. The molecular complex of claim 8 wherein the ligand is an asialoglycoprotein.

10. A method of forming a molecular complex for delivering a polynucleotide to a mammalian cell comprising:
    (a) contacting the carrier of claim 1 with the polynucleotide to be delivered under conditions which permit complexation of the carrier and the polynucleotide to form a molecular complex; and
    (b) recovering the molecular complex.

11. A method of claim 10 wherein the carrier comprises a conjugate of a ligand specific for the asialoglycoprotein receptor and polylysine.

* * * * *